United States Patent
Twerdochlib

[19]

[11] Patent Number: 6,094,989
[45] Date of Patent: Aug. 1, 2000

[54] METHOD AND APPARATUS FOR ANALYZING NON-SYNCHRONOUS BLADE VIBRATIONS USING UNEVENLY SPACED PROBES

[75] Inventor: Michael Twerdochlib, Oviedo, Fla.

[73] Assignee: Siemens Westinghouse Power Corporation, Orlando, Fla.

[21] Appl. No.: 09/138,187

[22] Filed: Aug. 21, 1998

[51] Int. Cl.[7] .................................................. G01N 29/00
[52] U.S. Cl. .................................. 73/659; 73/660; 702/56
[58] Field of Search ............................ 73/659, 660, 661; 702/56

[56] References Cited

U.S. PATENT DOCUMENTS

| | | | |
|---|---|---|---|
| 4,389,891 | 6/1983 | Fournier | 73/579 |
| 4,518,917 | 5/1985 | Oates et al. | 324/207 |
| 4,573,358 | 3/1986 | Luongo | 73/660 |
| 4,593,566 | 6/1986 | Ellis | 73/660 |
| 4,607,529 | 8/1986 | Morey | 73/660 |
| 4,996,880 | 3/1991 | Leon et al. | 73/660 |
| 5,148,711 | 9/1992 | Twerdochlib et al. | 73/660 |
| 5,206,816 | 4/1993 | Hill et al. | 73/660 |
| 5,471,880 | 12/1995 | Lang et al. | 73/660 |
| 5,610,339 | 3/1997 | Haseley et al. | 73/660 |
| 5,686,669 | 11/1997 | Hernandez et al. | 73/660 |
| 5,698,788 | 12/1997 | Mol et al. | 73/659 |

*Primary Examiner*—Hezron Williams
*Assistant Examiner*—Nashmiya Fayyaz
*Attorney, Agent, or Firm*—Eckert Seamans Cherin & Mellott, LLC

[57] ABSTRACT

Non-synchronous vibrations in blades on a rotating wheel, such as a turbine wheel, are measured using Fourier analysis adjusted to correct for uneven sampling produced by a pair of probes spaced from each other about the wheel by a probe angle (PA) other than 180°. The Fourier transform matrix is phase shifted by an amount which is a function of the PA which is other than 180°, and the harmonic in which the mode of non-synchronous vibration is expected to be found. A scaling factor in the form of an inverse correction factor is applied to the frequency spectra produced by the phase shifted Fourier transform matrix to generate an output representative of the frequency and amplitude of the true excitation frequency which can be presented on a display.

16 Claims, 9 Drawing Sheets

METHOD AND APPARATUS FOR ANALYZING NON-SYNCHRONOUS BLADE VIBRATIONS USING UNEVENLY SPACED PROBES

BACKGROUND OF THE INVENTION

1. Field of the Invention

This invention relates to determining the frequencies and amplitudes of non-synchronous vibration in the blades on a rotating wheel such as a turbine wheel, and specifically, to making such determinations where the probes detecting blade position are not evenly spaced about the wheel.

2. Background Information

The present invention has particular application to the detection of non-synchronous vibrations in the blades on a turbine wheel in a steam generator, but it will be appreciated that it can be applied to vibration analysis in other rotating systems.

Turbine blades, because of their complex design, are subject to vibration at frequencies which correspond to natural frequencies of the blades. Each natural frequency is associated with a particular mode, each of which is a different combination of vibrational deflections such as along the rotational axis of the turbine, perpendicular to the rotational axis of the turbine, and so forth. To prevent excessive vibration of the blade about its normal position, prudent design practice dictates that the blades be constructed such that the frequencies of the lowest modes fall between harmonics of the operating frequency of the turbine. However, the blades may be excited by non-synchronous forces such as aerodynamic buffeting or flutter. This may occur even if the natural resonance frequencies of the blade are not near the harmonics of the running speed of the turbine. When the amplitude of the vibration exceeds a certain level, objectional stresses are set up in the blade. If the condition is not detected and remedied, the blade may eventually fracture resulting in an extremely costly forced outage of the machinery. Thus, a method and apparatus for detecting non-synchronous vibration is useful to prevent such damage.

It is known to use non-contacting proximity sensors or probes to detect blade vibration. The probes detect the actual time of arrival of each blade as it passes each probe. The difference between the actual time of arrival of each blade and its expected time of arrival, determined with the use of an additional probe which tracks rotation of the turbine wheel, produces a signal containing blade vibration information. Fourier analysis is applied to this signal to extract the blade vibration frequencies and amplitudes.

Testing for synchronous vibrations is conducted by the manufacturer using a large number of probes, such as sixteen, which, in accordance with the Nyquist Theorem, yields unambiguous resolution of synchronous frequencies up to the eighth harmonic. Such tests for synchronous vibrations are carried out in test cells under conditions where the 16 probes can be evenly spaced about the turbine wheel.

In order to detect non-synchronous blade vibrations, a two probe blade vibration measurement system (BVM) is typically used. Under the Nyquist Theorem, such a system can only uniquely identify frequencies up to the fundamental rotational frequency of the rotor, and vibrations at this fundamental rotational frequency and its harmonics are all folded down onto each other and can be ignored. However, the non-synchronous vibrations, which are invariably above the system fundamental frequency, fold down into the first harmonic where they can be measured. Since there are only a few modes of non-synchronous vibration of interest, which can be predicted, the two probe system has been employed to measure non-synchronous blade vibrations even when the non-synchronous vibration frequencies are greater than the first harmonic frequency.

While the synchronous vibration tests are conducted under conditions where the probes can be evenly spaced, such is not the case for the non-synchronous vibration testing or monitoring. Typically, the two probe system is applied to a turbine on-line to monitor for non-synchronous vibrations induced by operating conditions. Under such circumstances it is common to find obstructions in the installation which prevent even spacing of even the two probes. While it is commonly understood that even sampling is necessary when performing a fast Fourier transform, it has commonly not been recognized as being a problem when utilizing a full Fourier transform as is used in BVM systems.

However, I have discovered that, in fact, uneven sampling does distort the results achieved using Fourier analysis in BVM systems having unevenly spaced probes, and thus in particular, two probe systems which commonly have unevenly spaced probes.

There is a need therefore, for improved methods and systems for measuring non-synchronous vibrations in blades on rotating wheels such as turbine wheels employing unevenly spaced probes.

In particular, there is a need for such improvement in methods and systems utilizing two unevenly spaced probes such as those used to measure non-synchronous blade vibrations.

SUMMARY OF THE INVENTION

These needs and others are satisfied by the invention which is directed to a method and apparatus for determining the frequencies and amplitudes of non-synchronous vibrations in the blades of a rotating wheel. In accordance with the invention, digital actual time of arrival signals representative of the actual time of arrival of the blades at probes which are spaced about the wheel by a probe angle other than 180° are processed using Fourier analysis adjusted for the probe angle other than 180° to generate outputs representative of the frequencies and amplitudes of the non-synchronous vibrations. More specifically, the digital actual time of arrival signals are processed to generate digital non-synchronous vibration signals such as by subtracting expected time of arrival signals for each blade from the actual time of arrival signals. A Fourier transform matrix is generated with a phase shift which adjusts for the probe angle other than 180°. In addition, a harmonic scaling factor which adjusts for the probe angle other than 180° is also generated. The Fourier transform matrix with the phase shift is then used to process the digitized non-synchronous vibration signals to generate digitized frequency spectra of the non-synchronous vibrations. The harmonic scaling factor is applied to the digitized frequency spectra to generate the output representative of the non-synchronous vibration.

Typically, the modes of non-synchronous vibrations will have frequencies above the fundamental rotational frequency $f_0$ of the wheel. Under these circumstances, an expected blade vibration mode having a fundamental frequency $f_n$ which is more than $f_0$ is selected. Based upon the expected vibration mode and the fundamental frequency of rotation of the wheel $f_0$, an excitation harmonic for the expected blade vibration mode is established. This excitation harmonic and the probe angle other than 180° are used to generate the Fourier transform matrix with the phase shift, which as stated previously, is then used to generate the digitized frequency spectra of the non-synchronous vibration. Following this, the excitation harmonic together with the probe angle is used to generate the scaling factor which is applied to the digitized frequency spectra to generate the representation of the non-synchronous vibration. These latter steps can be repeated for other selected vibration modes.

More particularly, the step of generating the Fourier transform matrix with the phase shift comprises generating Fourier basis vectors of the form:

sin (2π*FPA*i/revs−FTP)

cos (2π*FPA*i/revs−FTP)

where:
FPA=fractional probe angle=probe angle/360,
revs=number of wheel revolutions of data collected for digital time of arrival signals
FTP=π(n−(1−(−1)$^n$/2)(−1)$^n$(1−2*FPA),
n=sampling harmonic
i=Fourier series index In addition, the scaling factor is generated as an inverse correction factor (ICF) in the form:

ICF=|sin (π(2n−1)*FPA)|

Preferably, the probe angle other than 180° is selected so that only a selected expected blade vibration mode produces an output with a single peak. This feature can be applied to achieve a result not available with even sampling. By successively using the excitation harmonic for each of a plurality of expected modes of non-synchronous vibration to generate the phase shifted Fourier Transform Matrix and the scaling factor which are then used to generate outputs, the excited mode can be identified as the only mode which produces an output with a single peak.

Since the expected modes of vibration will rarely fold down to an exact sampling subharmonic, outputs for a plurality, such as three contiguous, subharmonics are generated to capture spectra leakage. These output subharmonics can be geometrically summed to produce a single amplitude which is associated with the subharmonic with the greatest amplitude, thus defining the frequency of the excited vibration mode.

Additionally, an alarm can be generated when any excited mode exceeds a predetermined threshold.

The invention also embraces apparatus for determining frequencies and amplitudes of non-synchronous vibrations in blades on a rotating wheel which includes: sensor means including a pair of probes spaced from each other about the wheel by a probe angle other than 180° generating data signals representative of the actual times of arrival of the blades at the probes. It further includes processing means processing the data signals using Fourier analysis adjusted to correct for the probe angle of other than 180° to generate outputs representing the frequencies and amplitudes of the non-synchronous vibrations. In a preferred form, the output means is a display device on which the non-synchronous vibration frequency spectra are displayed.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
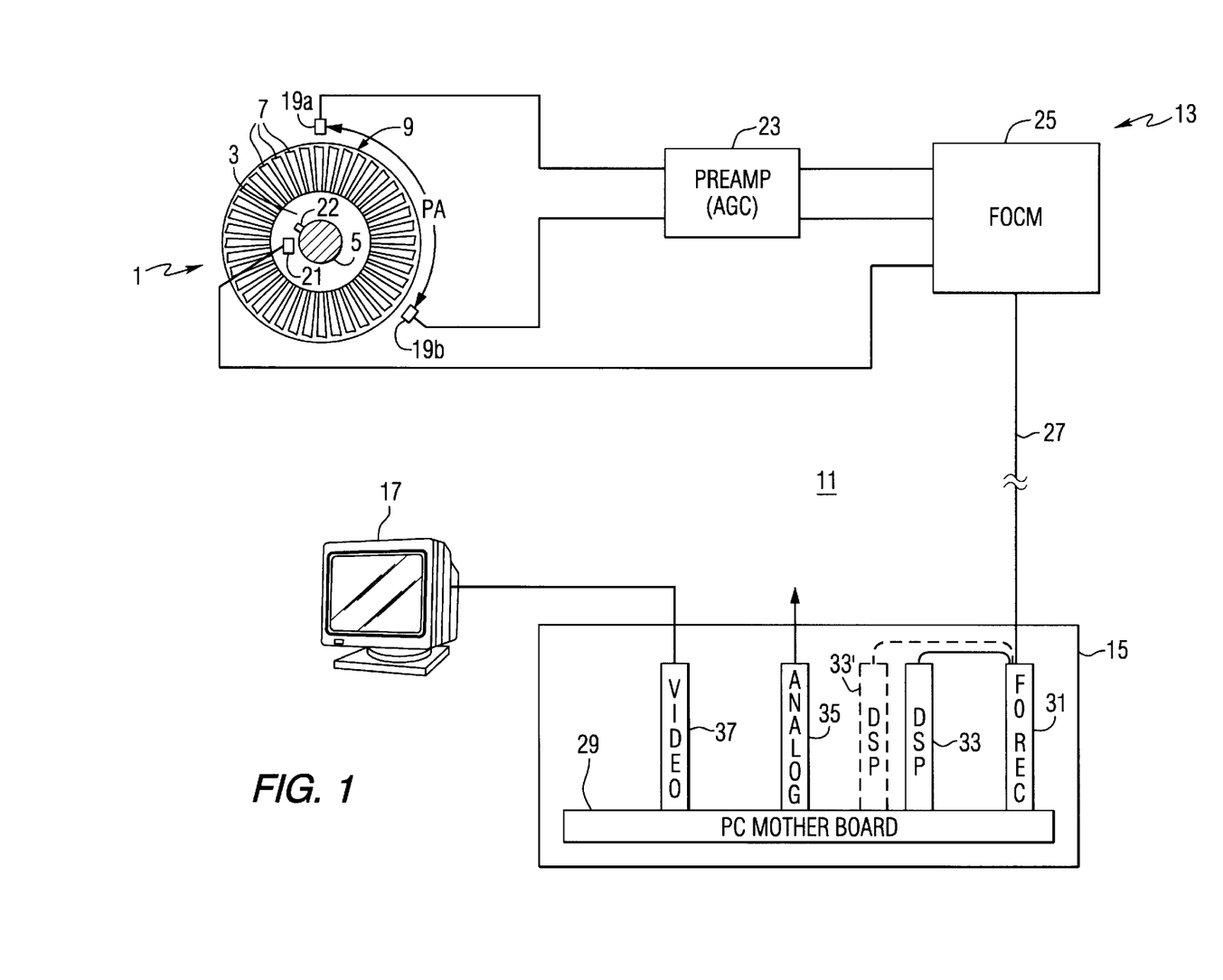
FIG. 1 is a schematic diagram of a system for determining the frequencies and amplitudes of non-synchronous vibrations of blades on a rotating wheel in accordance with the invention.

FIG. 1 illustrates a turbine wheel 1 having a rotor disk 3 mounted on a rotor shaft 5. A plurality of blades 7 are fixed to the periphery of the rotor disk 3 to form a row 9 of turbine blades. While only one row 9 of turbine blades is shown in FIG. 1, several similar rows of turbine blades mounted on rotor disks can be axially arranged along the rotor shaft 5.

In accordance with the invention, a blade vibration monitoring (BVM) system 11 is used to monitor for non-synchronous vibrations of the blades 7. The BVM system 11 is a two probe system. This system includes a sensor unit 13, a processing unit 15 and an output unit 17 in the form of a monitor.

The sensor unit 13 includes a pair of probes 19a and 19b spaced about the wheel 1 by a probe angle PA. The probes 19 are proximity sensors which detect the time-of-arrival (TOA) of each blade 7 at the probe as the wheel 1 rotates. Sensor unit 13 further includes a once-per-revolution probe 21 which senses a trigger device 22 mounted on the rotor. The probes 19 and 21 are proximity sensors which may be reluctance (magnetic), eddy current, laser, microwave or infrared probes depending upon specific test requirements and environmental conditions.

The analog actual (TOA) signals generated by the probes 19a and 19b are conditioned by a preamplifier 23 in the sensor unit which applies automatic gain control (AGC) to the analog signals. The conditioned actual (TOA) signals output by the preamplifier 23 and the once-per-revolution (OPR) signal generated by the probe 21 are applied to a fiber optic communications module (FOCM) 25. This module 25 which also forms part of the sensor unit 13 provides adjustment of signal amplitude and also establishes the trigger parameters for each signal. The signals generated by the probes 19 and 21 contain bipolar pulses. The trigger threshold is adjusted to occur at the highest slope associated with that part of the probe pass waveform. The arming threshold is used to prevent multiple triggering on the waveform.

The FOCM 25 includes an internal clock which in the exemplary system operates at 80 MHz. Each zero crossing in the three sensor signals causes the clock to be read. The time of each zero crossing along with a tag identifying the probe is transmitted by the FOCM to the processing unit 15, preferably over a fiber optic cable 27. In the exemplary system, data for increments of 32 revolutions of the shaft are processed. However, as discussed below, two revolutions of data are lost in filtering. Therefore, 34 revolutions of data are collected. This digital data is transmitted in a string of tag-clock numbers equal to [34*(number of blades)* (number of probes)+34] representing the time of arrival of each blade at each probe over the 34 revolutions and the 34 OPR signals.

The processing unit 15 includes a personal computer (PC) implemented on a personal computer mother board 29. Connected to the PC mother board is a fiber optic receiver board (FO REC) 31, a digital signal processor board (DSP) 33, an analog board 35 and a video board 37. The fiber optic receiver board 31 receives the digitally encoded light data signals from the sensor unit 13, converts them to digital electric signals and passes them on to the DSP board 33. The DSP board 33 performs processing on the data signals. The amount of processing performed by the DSP board 33 depends upon the capabilities of the PC. Typically, the DSP 33 determines the expected TOA for each blade from the OPR signal and subtracts the expected value from the actual value to generate a digital blade vibration signal for each blade. Also typically, a DSP board 33 is provided to process data for each row of blades, thus, if two rows of blades were to be monitored a second DSP board 33' would be added to the processor 15. Additional processing including Fourier analysis can be performed by the DSP although as the capabilities of PCs grow more of the processing is performed by the PC 29. The output of the Fourier analysis is frequency spectra for the non-synchronous vibrations. These frequency spectra can be processed by a video board 37 for presentation as a display on the monitor 17. As will be seen, additional outputs such as analog voltages and alarms can be generated. Such outputs are provided through an analog board 35.

The two probe BVM system 11 samples the vibration waveform of each blade 7 twice during each rotation of the rotor shaft 5. In the case of a machine operating at a rotor speed 3,600 rpm (60 Hz) this provides a sampling frequency of 120 Hz. This implies that vibration frequencies less than 60 Hz (120 Hz divided by 2) are unambiguously identified as taught by the Nyquist Theorem. This zero to 60 Hz frequency range (not including 60 Hz), is called the "first harmonic sampling range". The 60 Hz limit is called the "first sampling harmonic" which is also the "first harmonic of running speed" for a two probe system. It is common practice to refer to this frequency range and the frequency limit using the same term harmonic. In conventional vibration analysis, such as lateral shaft vibration, the analog vibration signal is filtered (with an anti-aliasing filter) to remove any frequency content in the vibration signal higher than the first sampling harmonic. With the anti-aliasing filter applied to the analog signal, any frequency content produced by taking the Fourier transform of the analog filter signal is then known to be within the first sampling harmonic range. If the anti-aliasing filter is set to 120 Hz (the second sampling harmonic), frequencies greater than the first harmonic are folded down into the first harmonic. Thus, for example, a 72 Hz excitation appears as a 60 Hz–(72 Hz–60)=48 Hz. The term fold is used to describe this apparent reflection about the first harmonic. Excitation in the third harmonic must be folded twice, i.e., reflected about the second, and then the first harmonic. For example, a 132 Hz excitation in the third harmonic is folded (reflected) about the second harmonic (120 Hz) to produce 108 Hz. Then this 108 Hz is folded (reflected) about the first harmonic (60 Hz) to produce the observed 12 Hz spectral line. With the anti-aliasing filter set at 120 Hz, however, this 132 Hz excitation would be removed and not seen in the first harmonic range.

The length (time) of the data array determines the resolution of the frequency measurement. If 32 revolutions of vibration data are analyzed by the Fourier transform, the first harmonic sampling range is divided into 32 subharmonics or frequency bins. In the 3,600 rpm example, the $n^{th}$ subharmonic or frequency bin represents $n*60/32=n*1.875$ Hz. The above analysis can be applied to other rotational frequencies of the rotor shaft. For example, at 1,800 rpm (30 Hz where the sampling frequency is 60 Hz), the $n^{th}$ subharmonic or frequency bin represents $n*30/32=n*3.750$ Hz.

Since blade vibration information generated by the sensor unit 13 is not analog, but sampled, it is not possible to filter the vibration signal as is commonly done for lateral shaft vibration. Folded or aliased excitations are observed. For the two probe BVM system 11, all observed excitations are aliased from higher harmonics (harmonic sampling ranges) since the blade mode frequencies are certainly greater than 60 Hz. Knowledge of the blade mode frequencies allows identification of the aliased blade vibration excitations observed in the first harmonic sampling range. For instance, consider a mode 1 excitation vibration at 204 Hz. This blade excitation frequency is in the $4^{th}$ harmonic, that is >180 Hz, but <240 Hz. Its position in the fourth harmonic is 204–180=24 Hz, which is nearest the 24/1.875=13 subharmonic. Folding down, reflecting about each harmonic, to the first harmonic, places the real mode near the 19th subharmonic in the first harmonic range. Similarly, a mode 2 excitation at 413 Hz folds down to the 28th subharmonic in the first harmonic range.

With two evenly spaced probes 19 (PA=180 degrees), uniform sampling of the vibration waveform is captured by the BVM 11. The Fourier transform of the resultant 120 Hz sampled data extracts the spectral content of the vibration waveform. A single sinusoidal excitation frequency produces a single spectral line.

Typically, a two probe BVM system 11 is used to monitor the blades of a turbine for non-synchronous vibrations caused by operating conditions. When monitoring an operational turbine, it is frequently not possible to evenly space the two blade sensing probes 19*a* and 19*b* due to obstructions. I have discovered that this spacing of the probes of a two probe system at a probe angle of other than 180 degrees results in errors in the Fourier spectra, but also offers some advantages.

Non-diametrically opposed probes 19*a* and 19*b* produce uneven sampling of the TOA data. For example, a PA of 136 degrees results in two sampling frequencies. One sampling frequency is equal to $(360/136) \times f_0$, and the other $(360/224) \times f_0$, where $f_0$ is the rotational frequency of the shaft. The assumption of uneven sampling is implicit in Fourier analysis through its use of the orthogonal sine and cosine mathematical functions as a functional or vector basis. When the vibration data is expanded in the Fourier functional basis (a Fourier transform is performed), the amplitude of each basis function (vector) represents the physical amplitude of the blade's vibration at that frequency depicted by each particular basis function. For example, if the resulting Fourier expansion the vibration data is:

$$42 \sin(\pi 6/32) \qquad \text{Eq. 1}$$

there is one vibration with an amplitude 42 and a frequency $(6/32) f_0$. In this example, data is collected over 32 revolutions of the shaft.

If vibration data is unevenly sampled, a single vibration motion cannot be expressed as a single basis function (vector) as in equation 1. In the latter case, two Fourier basis functions (or vectors) are required to represent the physical vibrational state of the blade. The second term is a phantom or ghost reflection. The physical interpretation of the amplitude of each Fourier basis vector as the amplitude of the physical vibration and the associated unique identification of the vibration frequency as equal to that of the Fourier vector is no longer realized. The Fourier expansion of the same physical vibration as depicted in equation 1, but with uneven sampling, would take the general form of:

$$9 \sin(\pi 6/32) + 34 \sin(\pi 26/32) \qquad \text{Eq. 2}$$

Figure 2:
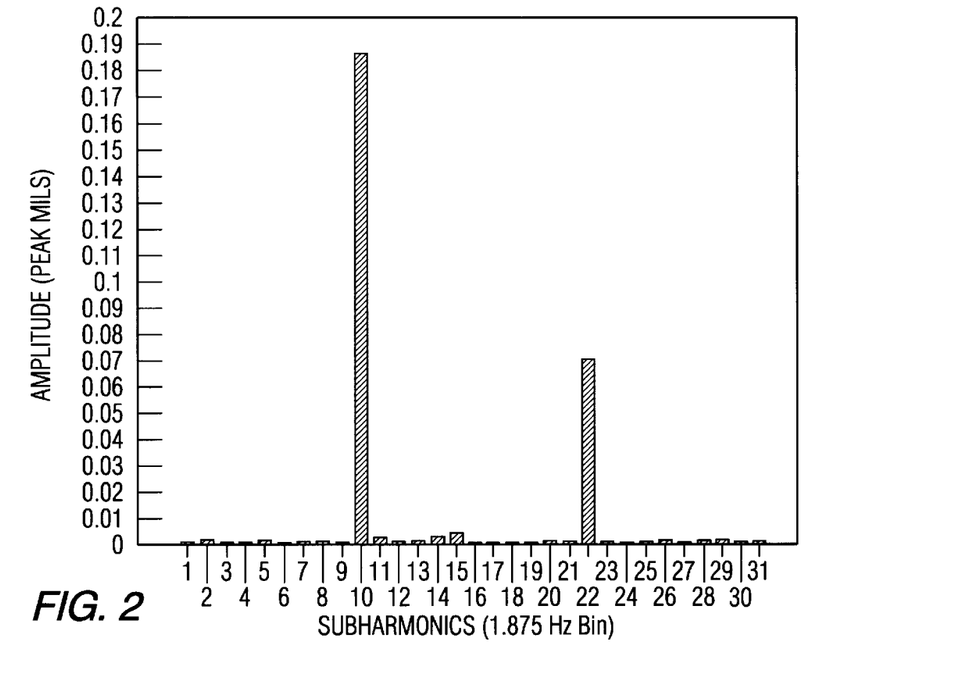
FIG. 2 is a display of the frequency spectra of a non-synchronous vibration showing the error produced by uneven sampling.

Another example of the effect of uneven sampling is shown in FIG. 2 where a single 200 mil peak excitation at 18.75 Hz (10th subharmonic) produces a phantom peak at the 22nd harmonic due to uneven sampling. The probe angle in this example was 136 degrees. Note that the uncorrected amplitude of the 10th subharmonic in FIG. 2 is 190 mils rather than the true 200 mils. In some instances, as in the example of equation 2, the ghost reflection will have a larger amplitude than the true frequency, and in some circumstances, only the ghost will be seen.

I have discovered a general method of unique redefinition of the Fourier basis vectors for each harmonic of the shaft rotation which preserves the one-to-one relationship between a redefined Fourier basis and the physical vibration amplitude and vibration frequency of the turbine blade as is realized in even sampling. Two distinct steps are carried out to correct the Fourier analysis of unevenly sampled data. In the first step, the Fourier basis vectors are redefined by introducing a phase shift (Fourier Transform Phasor or FTP) determined by the probe angle (PA) and the harmonic (n) in which the vibration excitation is present. For example, a 155 Hz blade vibration excitation would be in the 4th harmonic (n=4) for a shaft speed of 3,000 rpm.

The 2*revs Fourier basis vectors are transformed from:

$$\sin(2\pi FPA*i/revs)$$

$$\cos(2\pi(FPA*i/revs), \qquad \text{Eq. 3}$$

where:

FPA=Fractional Probe Angle=Probe Angle/360=180/360, and revs=number of revolutions of data collected (typically= 32)

i=Fourier index to:

$$\sin(2\pi FPA*i/revs - FTP)$$

$$\cos(2\pi(FPA*i/revs - FTP), \qquad \text{Eq. 4}$$

where:

FPA=Fractional Probe Angle=Probe Angle/360, and

FTP=$\pi(n-(1-(-1)^n)/2)(-1)^n(1-2*FPA)$

Figure 3:
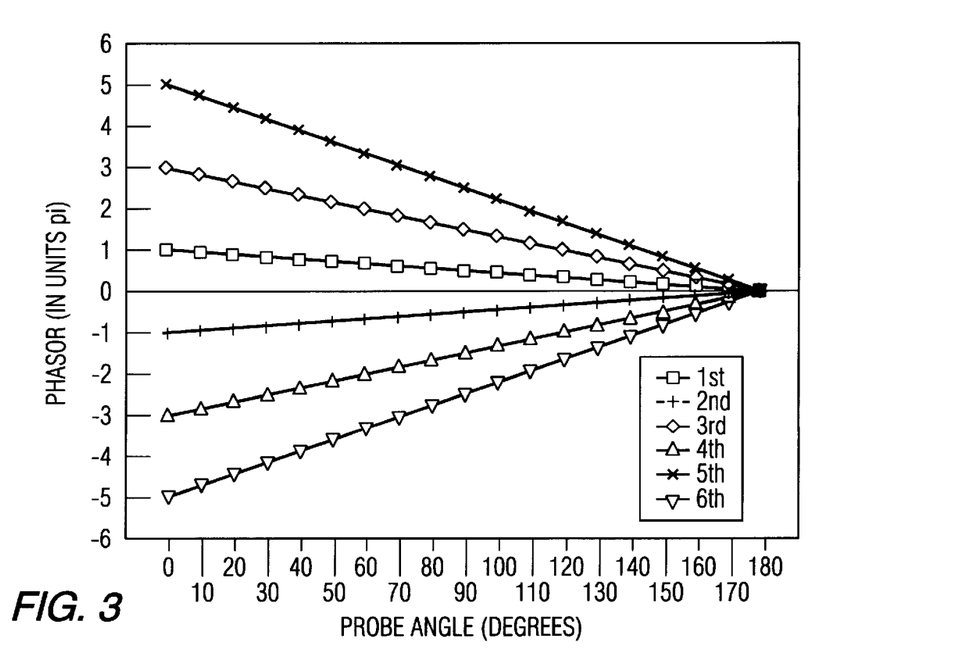
FIG. 3 illustrates the Fourier transform phasor for harmonics 1 through 6 for probe angles 0–180 degrees.

A plot of the Fourier Transform Phasors or FTPs for harmonics 1 through 6 is shown in FIG. 3. The FTPs reduce to 0 at Probe Angle=180 degrees where no correction is required. Corrections for probe angles greater than 180 degrees are also valid, but not shown.

As the second step of correcting the Fourier analysis of unevenly sampled data, a correction is applied to the vibration amplitude determined from the above FTP transform. The vibration amplitude obtained from the redefined Fourier basis vectors above is divided by the following Inverse Correction Factor (ICF):

$$ICF = |\sin(\pi(2n-1)*FPA)| \qquad \text{Eq. 5}$$

Figure 4:
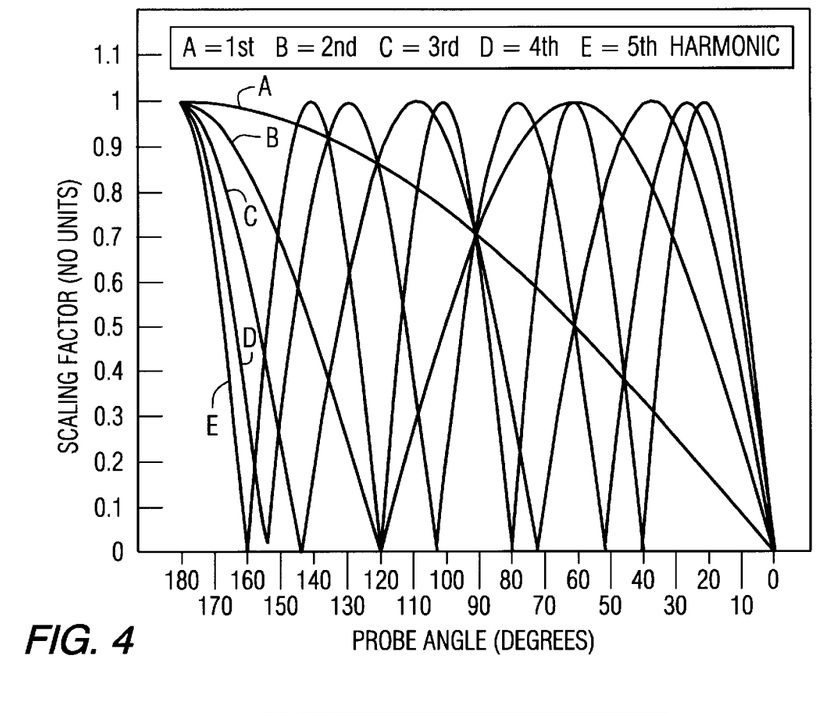
FIG. 4 illustrates the inverse correction factor for harmonics 1–5 for probe angles 0–180 degrees.
Figure 5:
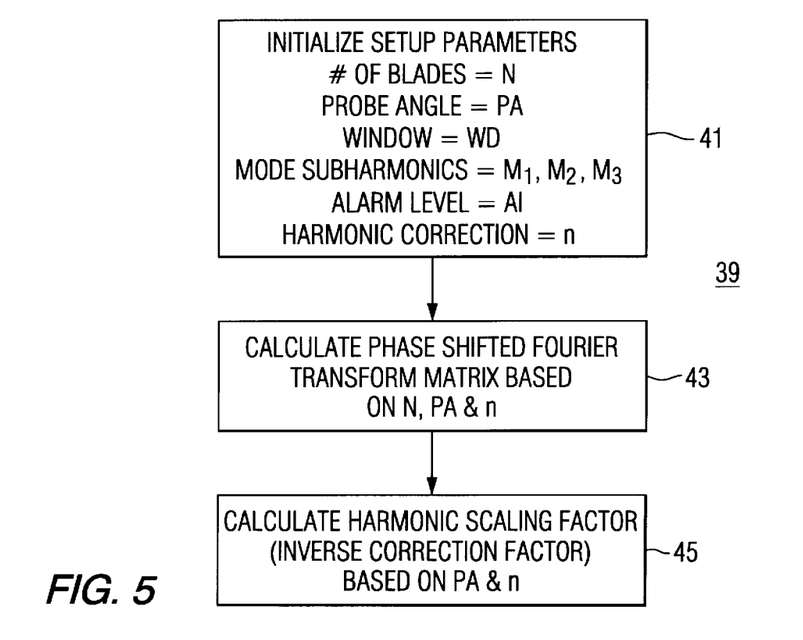
FIGS. 5, 6a–6c and 7 are flow charts illustrating implementation of the invention.

A plot of the Inverse Correction Factors or ICFs for harmonics 1 through 5 are shown in FIG. 4. All corrections converge to the value 1 as the Probe Angle approaches 180 degrees where no correction is required.

It should be noted that certain values of Probe Angle (PA) result in a unique correction for each harmonic. A double excitation response or phantom reflection is seen except when the proper harmonic correction is applied. Other PAs can uniquely unfold the excitation to a certain known harmonic. This occurs when all the FTPs cutting a vertical line drawn through the PA value on FIG. 4 differ from one another by values different from an integer times pi. A simple computer program can perform this task quite easily. This fact can be used to uniquely identify the folded vibration frequency. The potential identification (unfolding) of frequencies at and beyond the first harmonic of running frequencies is not possible for equal sampling as stated by the Nyquist Theorem. Also, it will be noted from FIG. 4 that the ICF has zero values for certain probe angles. No corrections are possible at or very near these points. These PAs should not be selected for the location of the blade probes.

FIGS. 5, 6a–6c and 7 illustrate flow charts used by the processor 15 to implement the invention. The software first enters a routine 39 shown in FIG. 5 in which the phase shifted Fourier transform and scaling (inverse correction) factor are determined. First, the parameters are initialized at 41. For simplicity the routine 39 assumes only one blade vibration mode and hence only one harmonic correction is made. As discussed previously, separate corrections must be developed for each mode. The parameters necessary include the number of blades, and the probe angle, which for uneven sampling will be other than 180 degrees. A window WD is then established as a tolerance for checking data, as will be explained. Since the frequency of the expected mode will most likely not fold down exactly onto a subharmonic in the first harmonic range, several contiguous subharmonics, for example three, M1, M2 and M3, are identified to capture spectra leakage. An alarm level, A1, which will be explained below, are also established. Finally, the harmonic correction n is established. Following initialization, the Fourier transform matrix is calculated at 37 using equation 3. The harmonic correction scaling factor is then calculated at 39 using equation 5.

Once the Fourier transform matrix is phase shifted and the scaling (inverse correction) factor has been calculated, the DSP is ready to process data. As shown in flowchart 47, beginning on FIG. 6a, the continuous streams of serial data from the probe 19a identified as s1, from the probe 19b identified as s2, and from the once-per-revolution probe 21 identified as OPR are sorted at 49 based on the appended tag. Data is collected for 34 revolutions as indicated at 51. The 34 revolutions worth of data for each probe is stored in an array at 53. Each of the s1 and s2 data arrays contains actual time of arrival information for each blade for each revolution. When 34 blocks of data have been accumulated, the data from that collection cycle is passed on at 55 for processing and a new cycle of 34 revolutions of data is initiated.

While a new cycle of data is being collected, the data from the last complete cycle passes to block 57 where the expected time of arrival for each of the blades at each of the serial probes is calculated using the OPR array data. The actual time of arrival of each blade at each probe is then subtracted from the corresponding expected time at block 59 in FIG. 6b to form difference arrays {delta s1} and {delta s2}. If the actual TOA is not found within a window WD centered about the expected time of arrival, the corresponding delta array element is labeled as bad.

Figure 6A:
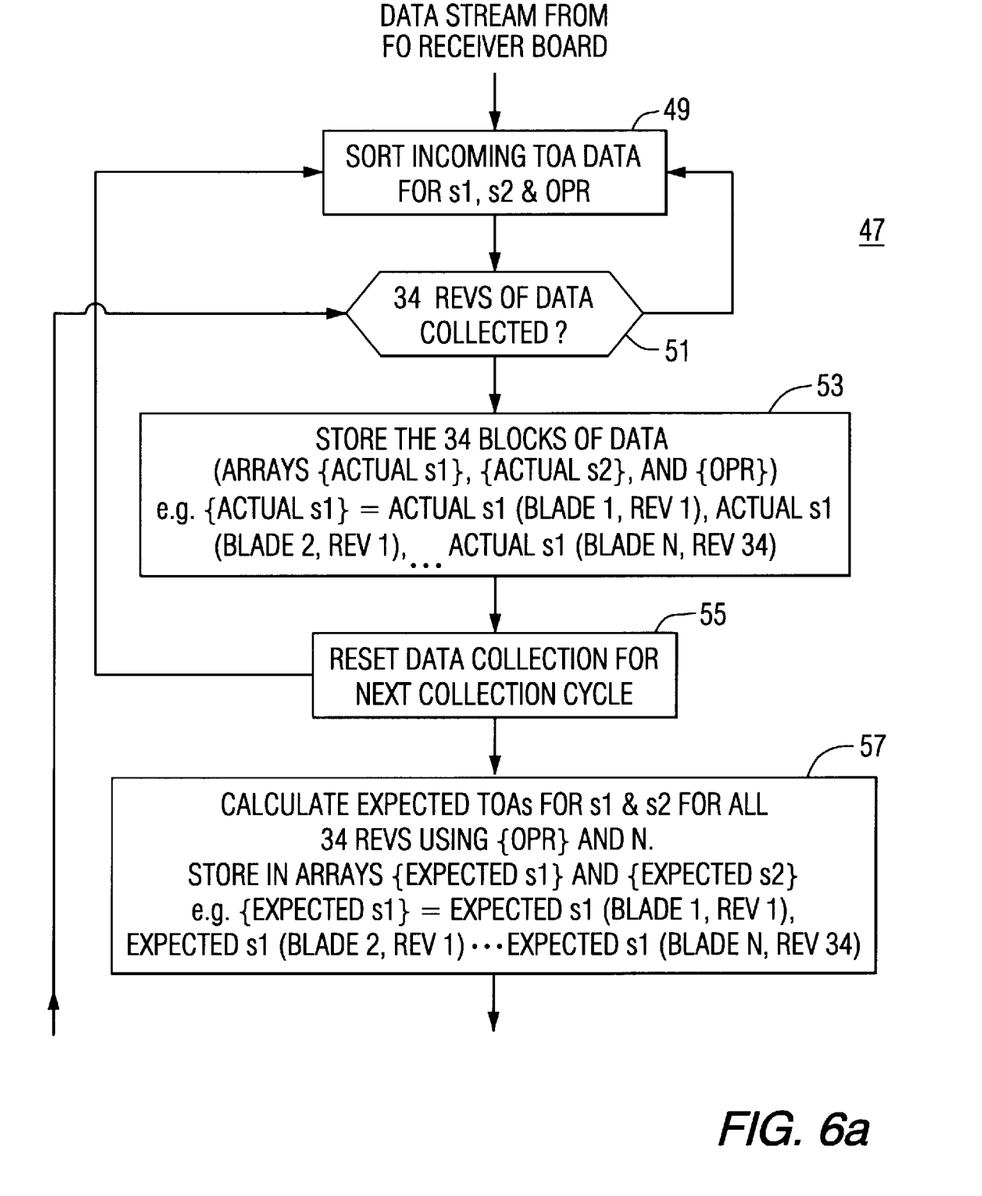
Figure 6B:
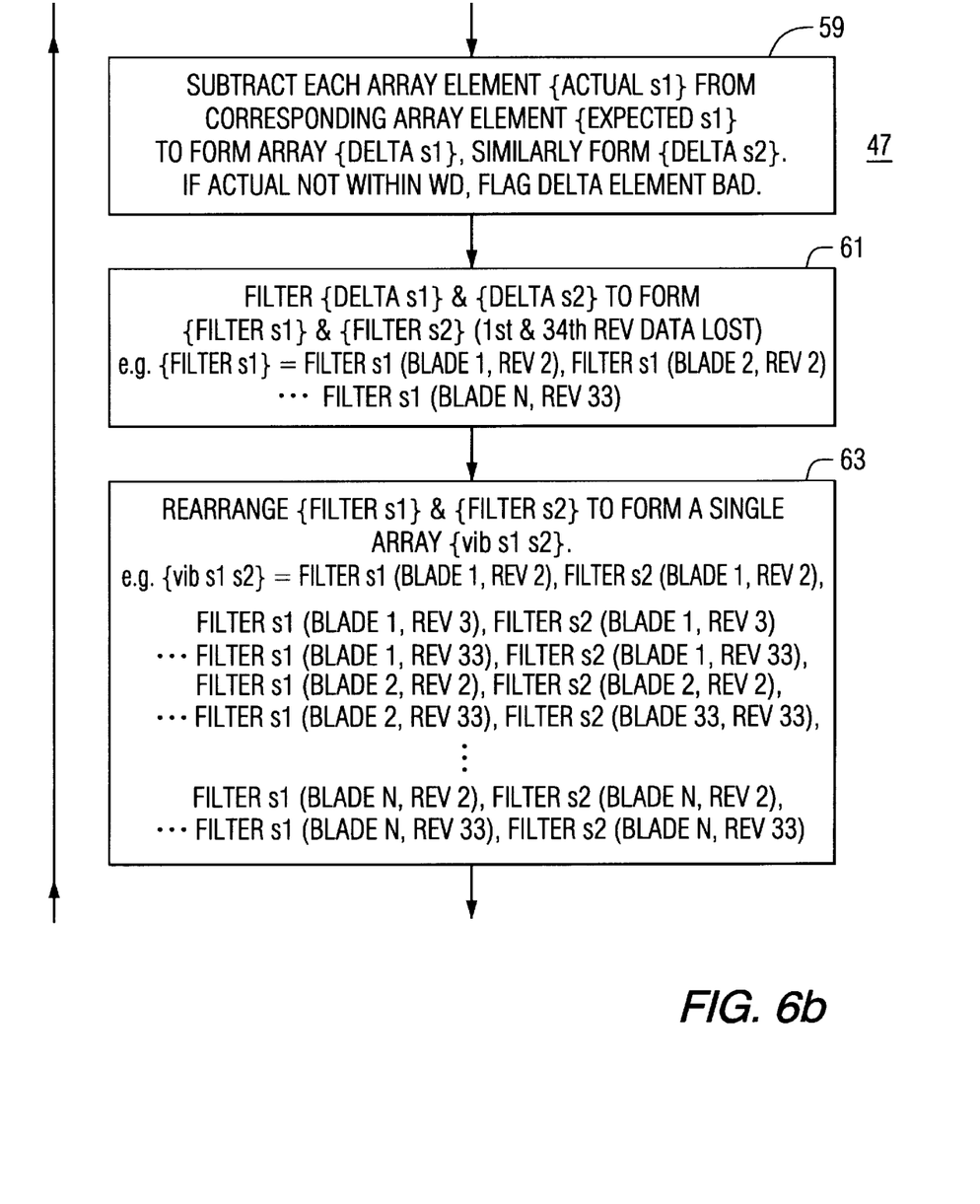
Figure 6C:
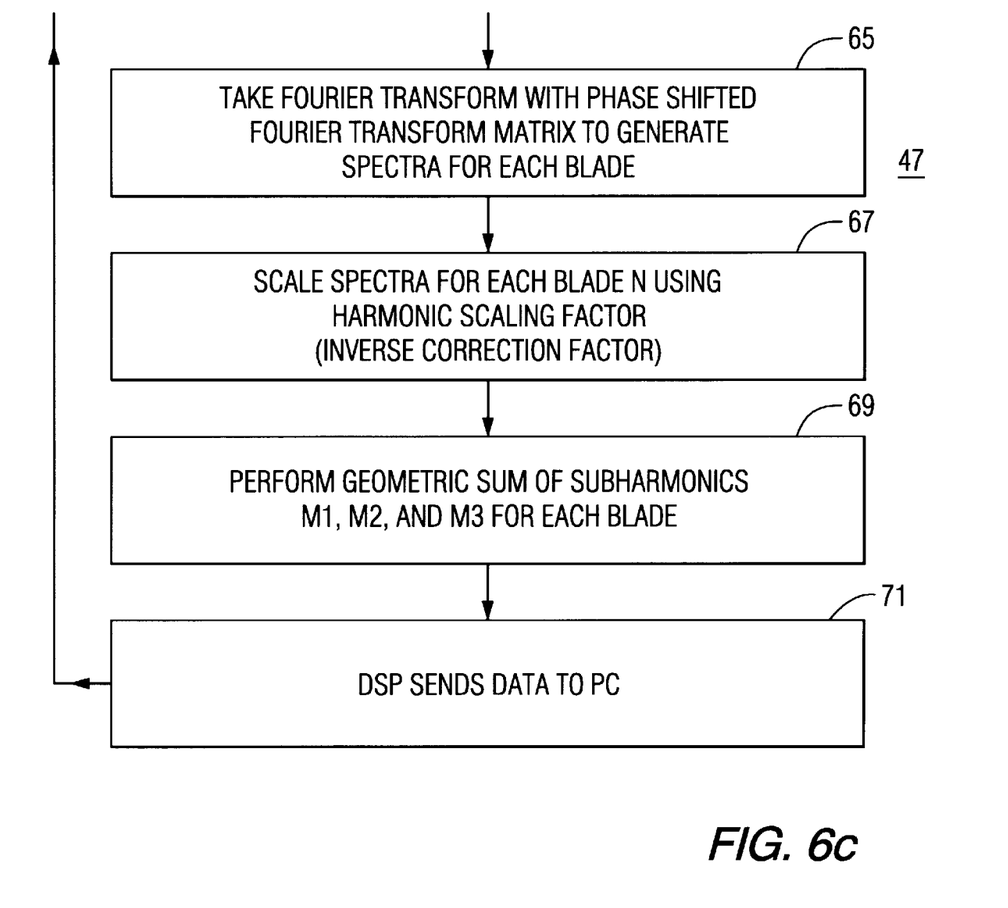

Next, the delta arrays are filtered at 61 to remove common mode motion such as those caused by torsion and speed changes. In this process, the first and thirty-fourth revolution data are lost so that 32 revolutions of data starting with the second actual revolution remain. The filter also corrects for the bad data in the delta arrays. This filtering technique is described in detail in U.S. Pat. No. 5,148,711.

Following filtering, the filtered data for the two serial probes 19a and 19b are rearranged at 63 to form a single array. The elements in this array {vibs1s2} are in the time sequence that each blade encounters a probe, whereas the elements in the {filter s1} and {filter s2} arrays are in time sequence that the probe s1 and the probe s2, respectively, encounter the blades.

The array {vibs1s2} contains a digital non-synchronous vibration signal for each blade. In order to extract the frequency and amplitude of the non-synchronous vibrations in these digital signals, the Fourier matrix with the phase shift previously calculated is applied to the elements of the array at 65 in FIG. 6c to generate a digitized spectra of the non-synchronous vibration for each blade. The scaling factor is then applied to the digitized spectra at 67 to generate outputs representing the non-synchronous vibration in each blade. A geometric sum (square root of sum of squares) of the subharmonics M1, M2, and M3 for each blade is then calculated at 69 to generate a composite vibration amplitude. The subharmonic with the largest amplitude is selected to identify the folded down expected modal frequency. The DSP sends the output information to the PC at 71 before looping back to similarly process the next cycle of 34 revolution data.

Figure 7:
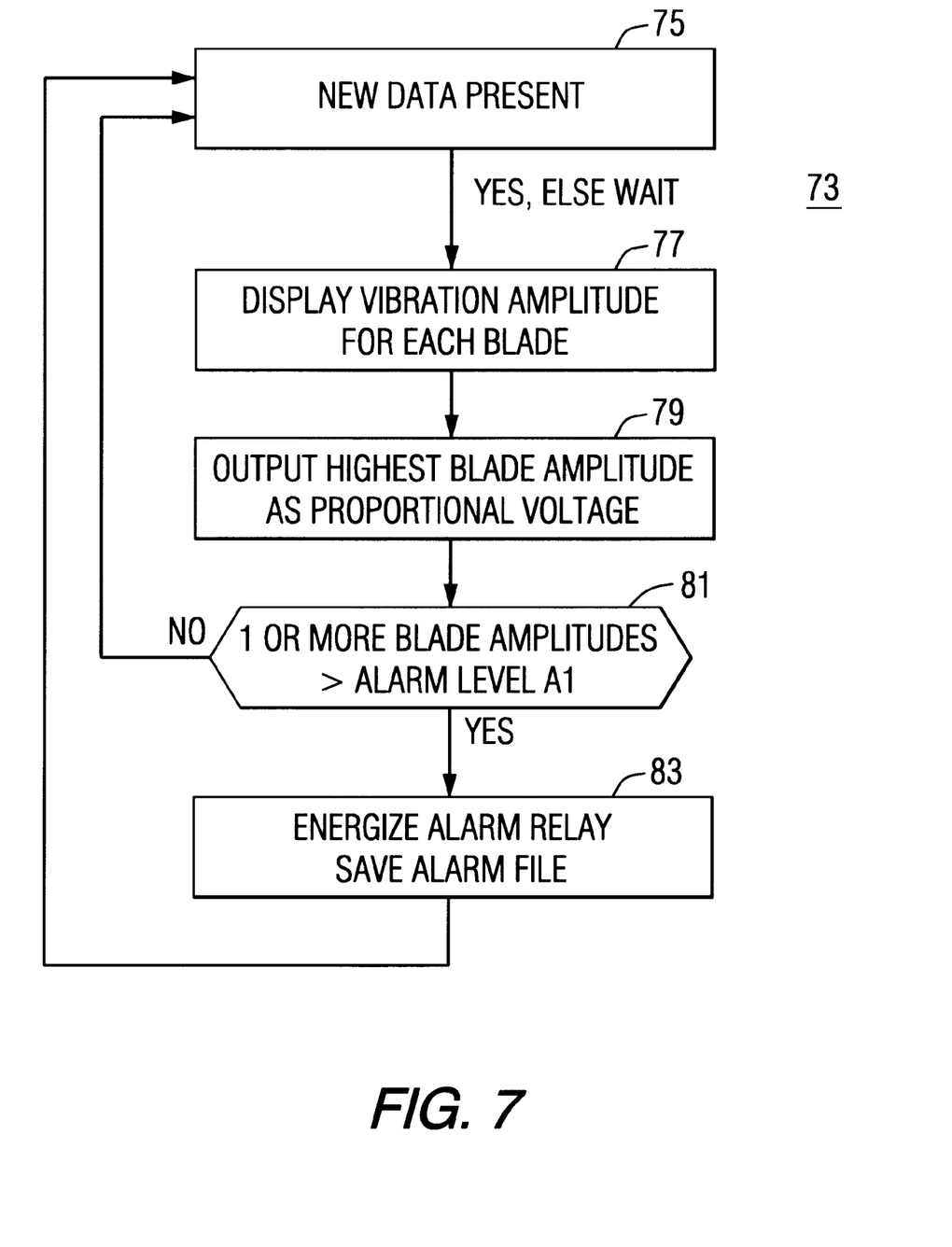

As shown in FIG. 7, the PC executes a routine 73 which looks for new data from the DSP at 75. When a new cycle of processed data is available, the PC sends through the video board 37 vibration amplitude for each blade for display on the monitor 17, as indicated at 77. The PC also outputs the highest blade amplitude as a proportional voltage through the analog board 35 as indicated at 79. Also, at 81, if any of the blade amplitudes exceed an alarm threshold, an alarm relay is energized and the alarm file is saved.

Figure 8:
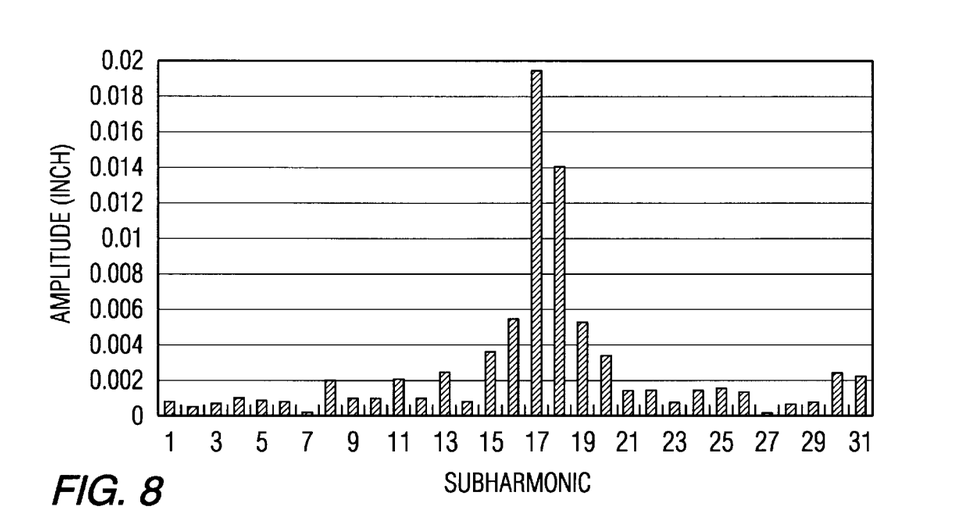
FIG. 8 illustrates a first example of a Fourier spectra distorted by uneven sampling.
Figure 9:
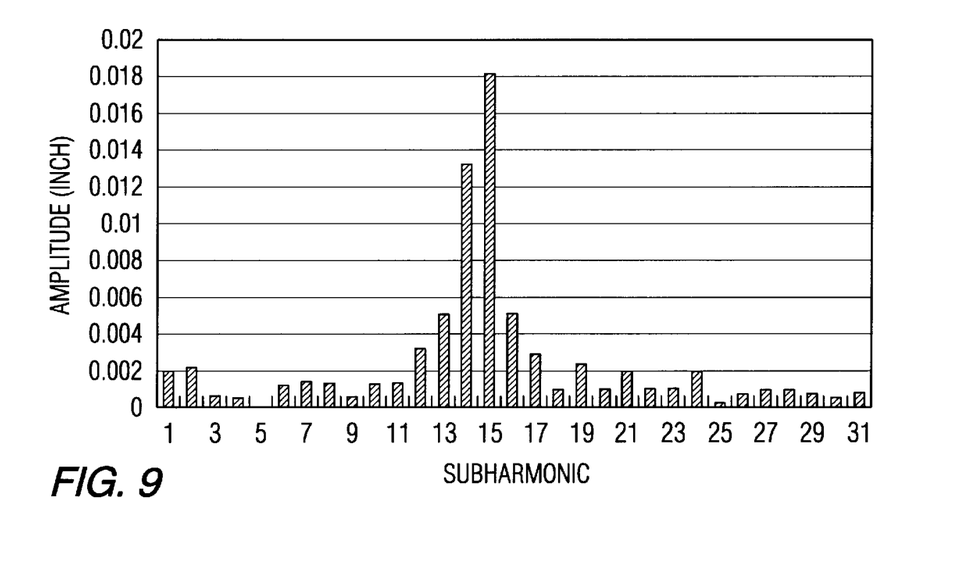
FIG. 9 illustrates the Fourier spectra of the example of FIG. 6 corrected for uneven sampling.

FIGS. 8 and 9 demonstrate application of the invention to real turbine blade data gathered through uneven sampling. FIG. 8 shows application of classical Fourier analysis without the invention applied to a high non-synchronous blade response. In this example, a 136 degree PA results in a single phantom peak at the 17th–18th subharmonic. This phantom peak was subsequently used to evaluate blade performance. In this example, the real peak at the 14th–15th subharmonic, is not evidenced.

FIG. 9 shows application of Fourier analysis adjusted in accordance with the invention to the same blade data as in FIG. 8. As demonstrated, the real peak at the 14th–15th subharmonic is correctly detected by use of the invention.

Figure 10:
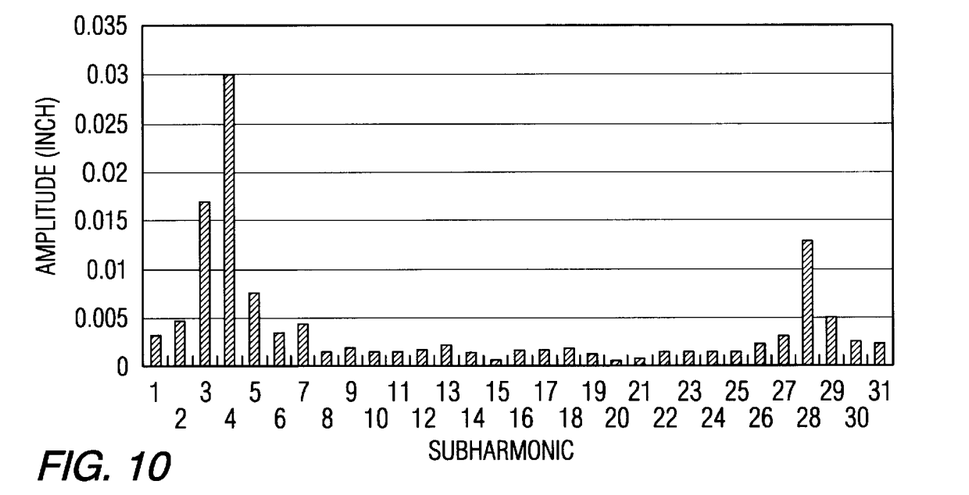
FIG. 10 illustrates a second example of non-synchronous vibrations distorted by uneven sampling to generate a real and a phantom excitation frequency.
Figure 11:
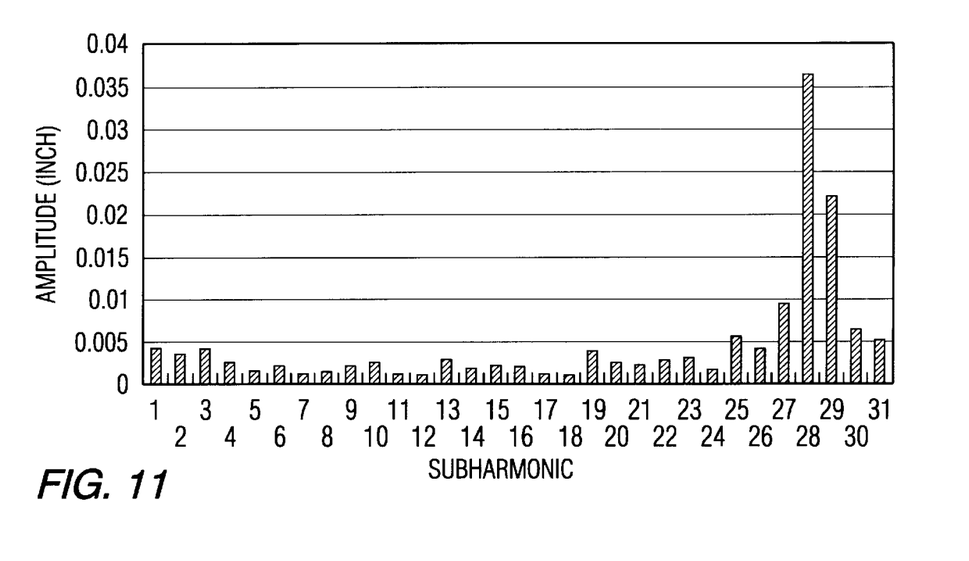
FIG. 11 illustrates the frequency spectra of FIG. 8 corrected for uneven sampling in accordance with the invention.

FIGS. 10 and 11 show the effect of the application of the invention to a BVM system in which uneven sampling is performed with the two probes at a PA of 143.2 degrees. In this example, a real excitation and phantom excitation are produced by the uneven sampling. The phantom excitation at the 3rd–4th subharmonic is greater in amplitude than the real excitation at the 28th–29th harmonic. By applying harmonic correction 1 through 8, only harmonic 2, 4 and 7 remove the double peak. The second harmonic is lower in frequency than predicted by static measurement. Excitations in the 7 harmonic do not generally produce high tip deflection. Hence, harmonic 4 is identified as the most likely excitation harmonic and the excitation is unfolded as 3×50 Hz+4×(50/32) Hz or the 28th subharmonic for this 50 Hz unit. The probe angle PA can be selected so that the unfolding will be unique in the manner discussed above in connection with FIG. 3.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A method of determining frequencies and amplitudes of non-synchronous vibrations in blades on a rotating wheel using a pair of probes spaced from each other about said wheel by a probe angle other than 180°, said method comprising the steps of:

generating from said probes digital actual time of arrival signals representative the actual times of arrival of said blades at said probes; and processing said digital actual time of arrival signals using Fourier analysis adjusted for said probe angle other than 180° to generate outputs representative of said frequencies and amplitudes of said non-synchronous vibrations.

2. The method of claim 1 wherein said processing comprises:

a) initially processing said digital time of arrival signals to generate digital non-synchronous vibration signals;

b) generating a Fourier transform matrix with a phase shift which adjusts for said probe angle other than 180°;

c) generating a harmonic scaling factor which adjusts for said probe angle other than 180°;

d) generating from said digitized non-synchronous vibration signals using said Fourier transform matrix with said phase shift, digitized frequency spectra of said non-synchronous vibrations; and e) applying said harmonic scaling factor to said digitized frequency spectra to generate said outputs representative of said frequencies and amplitudes of said non-synchronous vibrations.

3. The method of claim 2 wherein said wheel has a fundamental rotational frequency, $f_0$, and said steps of generating said Fourier transform matrix and generating said scaling factor comprise:

a) selecting an expected blade vibration mode having a fundamental frequency $f_m$ which is more than $f_0$;

b) establishing, based upon $f_0$ and $f_m$, an excitation harmonic for the expected blade vibration mode;

c) using said excitation harmonic together with said probe angle other than 180° to generate said Fourier transform matrix with said phase shift; and d) using said excitation harmonic together with said probe angle to generate said scaling factor.

4. The method of claim 3 comprising selecting another expected blade vibration mode having another fundamental frequency $f_m$ greater than $f_0$ and repeating steps b) through d) of claim 3.

5. The method of claim 3 wherein said step of generating said Fourier transform matrix with said phase shift comprises generating Fourier basis vectors of the form:

$$\sin(2\pi*FPA*i/\text{revs}-FTP)$$

$$\cos(2\pi*FPA*i/\text{revs}-FTP)$$

where:

FPA=fractional probe angle=probe angle/360, revs=number of wheel revolutions of data collected for digital time of arrival signals $FTP=\pi(n-(1-(-1)^n/2)(-1)^n(1-2*FPA)$, n=sampling harmonic i=Fourier series index.

6. The method of claim 5 wherein said scaling factor is generated as an inverse correction factor (ICF) in the form:

$$ICF=|\sin(\pi(2n-1)*FPA)|.$$

7. The method of claim 3 including selecting the probe angle other than 180° so that only said expected blade vibration produces an output with a single peak.

8. The method of claim 3 including establishing a plurality of subharmonics for said expected mode and repeating steps d) and e) of claim 2 to generate an output for each of said subharmonics.

9. The method of claim 8 including generating a composite output which is a geometric sum of said outputs for each of said subharmonics.

10. The method of claim 9 wherein said plurality of subharmonics comprises three consecutive subharmonics.

11. The method of claim 9 wherein said composite output is identified with a one of the plurality of subharmonics having the greatest amplitude.

12. The method of claim 7 adapted for identifying an excited mode of non-synchronous vibration comprising successively using an excitation harmonic for each of a plurality of expected modes of non-synchronous vibration to generate said Fourier Transform Matrix with said phase shift and said scaling factor, generating said outputs for each expected mode using the successively generated Fourier Transform Matrix with said phase shift and said scaling factor, and identifying the excited mode from the only output with said single peak.

13. The method of claim 2 including generating an alarm when an amplitude of a non-synchronous vibration exceeds a predetermined threshold.

14. Apparatus for determining frequencies and amplitudes of non-synchronous vibrations in blades on a rotating wheel, comprising:

sensor means including a pair of probes spaced from each other about said wheel by a probe angle other than 180° for generating data signals representative of actual times of arrival of said blades at said probes;

processing means processing said data signals using Fourier analysis adjusted to correct for said probe angle of other than 180° to generate outputs representing said frequencies and amplitudes of said non-synchronous vibrations; and output means presenting said outputs representing said non-synchronous vibrations.

15. The apparatus of claim 14 wherein said output means comprises a monitor on which said outputs are displayed.

16. The apparatus of claim 14 wherein said output means comprises alarm means generating an alarm indication when an output exceeds a predetermined threshold.

* * * * *